(12) United States Patent
Suri

(10) Patent No.: US 10,499,941 B2
(45) Date of Patent: Dec. 10, 2019

(54) MITRAL VALVE REPAIR DEVICES

(71) Applicant: Mayo Foundation for Medical Education and Research, Rochester, MN (US)

(72) Inventor: Rakesh M. Suri, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 487 days.

(21) Appl. No.: 14/651,793

(22) PCT Filed: Dec. 13, 2013

(86) PCT No.: PCT/US2013/075082
§ 371 (c)(1),
(2) Date: Jun. 12, 2015

(87) PCT Pub. No.: WO2014/093861
PCT Pub. Date: Jun. 19, 2014

(65) Prior Publication Data
US 2015/0313620 A1    Nov. 5, 2015

Related U.S. Application Data

(60) Provisional application No. 61/737,418, filed on Dec. 14, 2012.

(51) Int. Cl.
*A61B 17/29* (2006.01)
*A61F 2/24* (2006.01)
(Continued)

(52) U.S. Cl.
CPC .......... *A61B 17/29* (2013.01); *A61B 17/0401* (2013.01); *A61B 17/0643* (2013.01);
(Continued)

(58) Field of Classification Search
CPC .... A61F 2/2454; A61F 2/2457; A61F 2/2463; A61F 2/24; A61F 2/2427; A61F 2/2487;
(Continued)

(56) References Cited

U.S. PATENT DOCUMENTS 7,632,308 B2    12/2009  Loulmet
2003/0105519 A1 *  6/2003  Fasol ................... A61F 2/2457
                                                       623/2.1
(Continued)

FOREIGN PATENT DOCUMENTS

WO    WO2012040865 A2    4/2012
WO    WO2012167120 A2    12/2012

OTHER PUBLICATIONS

Grossman and Baim. Grossman's Cardiac Catheterization, Angioplasty, and Intervention: 6th Edition. Sep. 28, 2000. Chapter 4.*
(Continued)

*Primary Examiner* — Todd J Scherbel
*Assistant Examiner* — Brooke Labranche
(74) *Attorney, Agent, or Firm* — Fish & Richardson P.C.

(57) ABSTRACT

This document provides devices and methods for repairing a prolapsing mitral valve leaflet using minimally invasive catheter based approaches. For example, percutaneous procedures that involve folding and securing a segment of a prolapsing leaflet onto or pulling and securing a segment of a prolapsing leaflet through part of the greater mitral valve leaflet are provided. In some cases, artificial chordae are installed to stabilize and maintain desired orientation of the leaflets.

9 Claims, 18 Drawing Sheets

(51) Int. Cl.
  *A61B 17/04* (2006.01)
  *A61B 17/064* (2006.01)
  *A61B 17/068* (2006.01)
  *A61B 17/122* (2006.01)
  *A61B 17/00* (2006.01)

(52) U.S. Cl.
  CPC ........ *A61B 17/0686* (2013.01); *A61F 2/2457* (2013.01); *A61B 17/0485* (2013.01); *A61B 17/122* (2013.01); *A61B 2017/00243* (2013.01); *A61B 2017/00349* (2013.01); *A61B 2017/0408* (2013.01); *A61B 2017/0409* (2013.01); *A61B 2017/0417* (2013.01); *A61B 2017/0419* (2013.01); *A61B 2017/2905* (2013.01); *A61F 2/2487* (2013.01)

(58) Field of Classification Search
  CPC ...... A61B 2017/00243; A61B 17/0485; A61B 2017/00349; A61B 17/29; A61B 17/0401; A61B 17/0643; A61B 17/0686; A61B 17/122; A61B 2017/0408; A61B 2017/0409; A61B 2017/0417; A61B 2017/0419; A61B 2017/2905
  See application file for complete search history.

(56) References Cited

U.S. PATENT DOCUMENTS

| | | |
|---|---|---|
| 2007/0118151 A1 | 5/2007 | Davidson |
| 2008/0195126 A1 | 8/2008 | Salem |
| 2009/0105751 A1* | 4/2009 | Zentgraf ............ A61B 17/0469 606/206 |
| 2009/0118744 A1 | 5/2009 | Wells et al. |
| 2010/0023118 A1 | 1/2010 | Medlock et al. |
| 2010/0042147 A1 | 2/2010 | Janovsky et al. |
| 2010/0049311 A1 | 2/2010 | Loulmet |
| 2010/0161042 A1 | 6/2010 | Maisano et al. |
| 2010/0179574 A1 | 7/2010 | Longoria et al. |
| 2011/0230962 A1 | 9/2011 | Moaddeb et al. |
| 2011/0264208 A1 | 10/2011 | Duffy et al. |
| 2012/0330407 A1* | 12/2012 | Dale ..................... A61B 17/122 623/2.11 |

OTHER PUBLICATIONS

International Search Report and Written Opinion for PCT/US2013/075082 dated Mar. 27, 2014, 7 pages.
International Preliminary Report on Patentability for PCT/US2013/075082, dated Jun. 25, 2015, 7 pages.

\* cited by examiner

MITRAL VALVE REPAIR DEVICES

CROSS-REFERENCE TO RELATED APPLICATIONS

This application is a National Stage application under 35 U.S.C. § 371 of International Application No. PCT/US2013/075082, having an International Filing Date of Dec. 13, 2013, which claims the benefit of U.S. Provisional Application Ser. No. 61/737,418, filed Dec. 14, 2012. The disclosure of the prior applications are considered part of (and are incorporated by reference in) the disclosure of this application.

BACKGROUND

1. Technical Field

This document relates generally to medical devices and particularly to a system and method for treating mitral valve regurgitation of all etiologies, and particularly degenerative mitral regurgitation due to leaflet prolapse caused by ruptured (flail) or elongated chordae tendineae.

2. Background Information

The mitral valve controls blood flow between the receiving and ejecting chambers of the left side of the heart, i.e., the left atrium and left ventricle. With each heartbeat, the atrium contracts to push blood into the ventricle. The leaflets of the mitral valve open to let the blood through. A properly functioning mitral valve allows blood to flow from the left atrium into the left ventricle, but not the other way. The mitral valve consists of two leaflets (anterior and posterior) attached to a fibrous ring or annulus. When the ventricle contracts to pump the blood out of the heart, the leaflets of the mitral valve close and create one of the highest pressure chambers in the body. In a healthy heart, the mitral valve leaflets overlap during contraction of the left ventricle to form a tight seal that prevents blood from flowing back into the atrium.

SUMMARY

This document provides devices and methods for repairing a prolapsing mitral valve leaflet using minimally invasive catheter based approaches. The procedures generally involve a percutaneous "foldoplasty," where a segment of a prolapsing leaflet is folded/pulled onto the atrial or ventricular surface of the greater mitral valve leaflet and secured. This procedure can include the following general steps. A prolapsing posterior leaflet can be approached using a minimally invasive and/or catheter-based approach. In some cases, the leaflet can be pierced to orient the grasping device. The prolapsing segment of the leaflet is captured. The prolapsing segment of the leaflet can be repositioned so as to support it and reduce or eliminate regurgitation. The prolapsing segment of the leaflet can be secured into the repositioned configuration. In some cases, an artificial chordae can be installed to further stabilize/support the leaflet.

In general, one aspect of this document features methods for treating mitral valve prolapse of a mammal. A method for treating mitral valve prolapse of a mammal comprises forming a channel through at least a portion of a mitral valve leaflet, and feeding at least a portion of the mitral valve leaflet through the channel. The method can include securing the portion of the mitral valve leaflet to other cardiac structures utilizing sutures, screws, anchors, and the like.

The foregoing and other embodiments can each optionally include one or more of the following features, alone or in combination. The mammal may be a human. The channel may extend from an atrial side surface of the mitral valve to a ventricle side surface of the mitral valve. A device comprising a grasper may be used to form the channel. The device may be extended through the channel and the grasper may be used to grasp an edge of the mitral valve. The device may be withdrawn from the channel while the grasper is grasping the edge of the mitral valve, and an anchor may be used to position or retain the edge of the mitral valve leaflet in relation to the channel. The anchor may be a suture or a clip device. In general, another aspect of this document features a method for treating mitral valve prolapse comprising approaching a prolapsed leaflet using a minimally invasive catheter technique, capturing a segment of the prolapsed leaflet using a grasping device, repositioning the segment on or against another portion of the prolapsed leaflet, and securing the segment to the other portion of the prolapsed leaflet using an attachment device. In some embodiments, the mitral valve leaflet may be constrained in a folded configuration as a result of applying the anchor.

In general, another aspect of this document features a method for treating mitral valve prolapse comprising approaching a prolapsed leaflet using a minimally invasive catheter technique, piercing the prolapsed leaflet using an anchor device, securing a first end of the anchor device to the prolapsed leaflet, applying tension to the anchor device, and securing a second end of the anchor device to the prolapsed leaflet. In some embodiments, the mitral valve leaflet may be constrained in a folded configuration as a result of as a result of the securing the segment using the attachment device.

In general, another aspect of this document features a method for treating mitral valve prolapse comprising approaching a prolapsed leaflet using a minimally invasive catheter technique, piercing the prolapsed leaflet using an anchor device, securing a first end of the anchor device to the prolapsed leaflet, applying tension to the anchor device, and securing a second end of the anchor device to a non-mitral valve area. In some embodiments, the prolapsed leaflet may be constrained in a folded configuration as a result of the securing the first and second ends of the anchor device to the prolapsed leaflet.

In general, another aspect of this document features a method for treating mitral valve prolapse comprising approaching, using a minimally invasive catheter technique, a prolapsed mitral valve leaflet via an interatrial septum or interventricular septum of the heart, applying a clip onto the prolapsed leaflet, wherein an edge of the prolapsed mitral valve leaflet is constrained in a folded configuration as a result of applying the clip, and wherein an artificial chordae is attached at a first end to the clip, and anchoring a second end of the artificial chordae to an area of the heart.

The foregoing and other embodiments can each optionally include one or more of the following features, alone or in combination. The tension of the artificial chordae may be adjusted while monitoring one or more characteristics of the heart such as a level of regurgitation of the mitral valve. Optionally, the clip may be a two-piece clip. In some embodiments, the method can further comprise attaching a first end of a second artificial chordae to the clip and attaching a second end of the second artificial chordae to another area of the heart.

Particular embodiments of the subject matter described in this specification can be implemented so as to realize one or more of the following advantages. In some embodiments, prolapsed mitral valve leaflets can be treated using minimally invasive treatment techniques. As such, surgery risks in comparison to open-chest surgery can be mitigated;

patient recovery and dismissal from hospital can be expedited; and risks of complications such as secondary infections can be reduced. Patients who are not candidates for open-chest surgery due to the associated risks may be able to receive treatment for a prolapsing mitral valve condition using the systems and techniques provided herein. Early quality of life and return to work can be improved following minimally invasive mitral valve repair. The personal and societal cost associated with this therapy may be more favorable due to resumption of normal daily activities and employment within a short period of time following percutaneous mitral valve repair.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
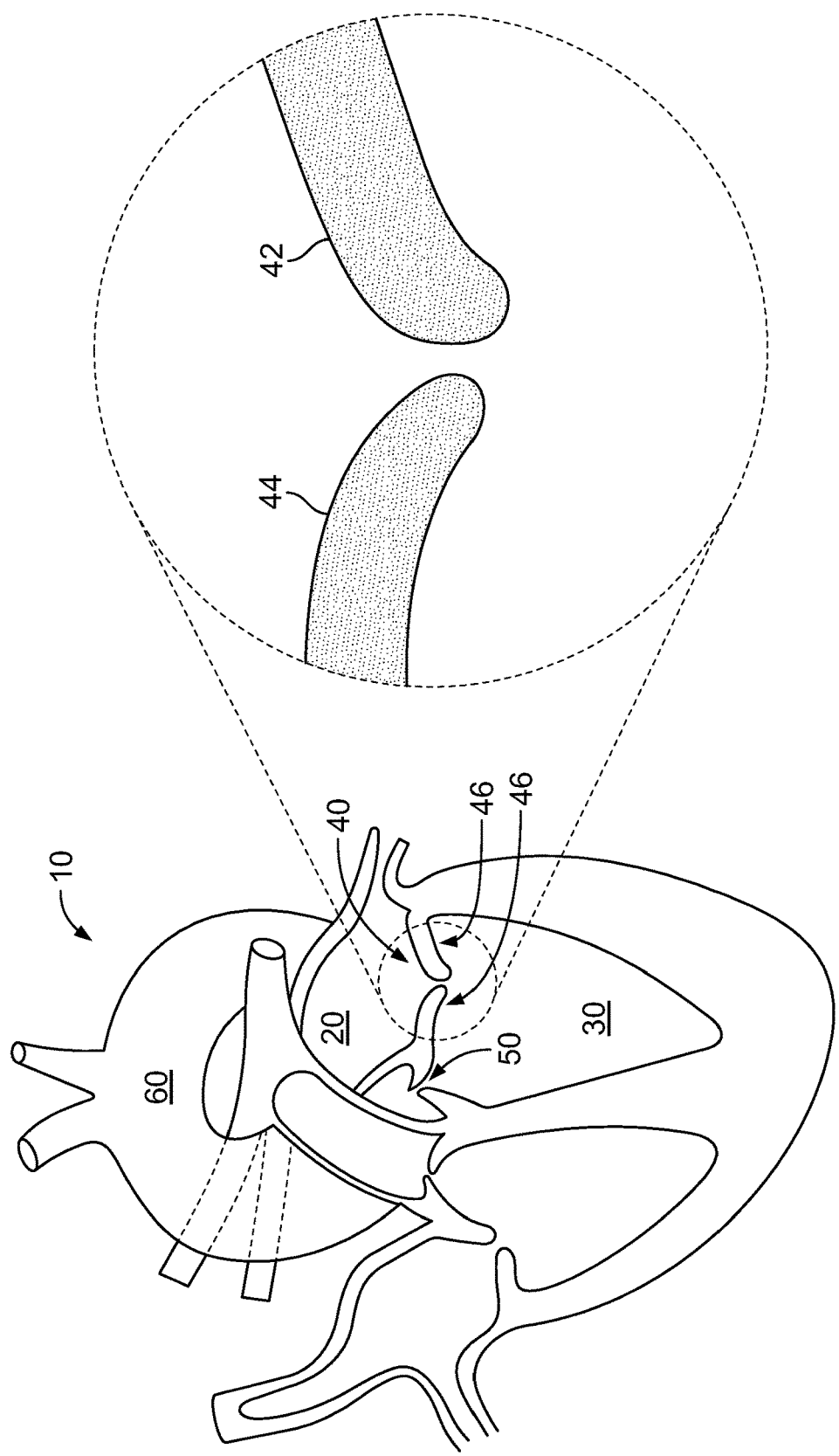
FIG. 1 is a schematic cross-section of a heart with a close-up view of the mitral valve leaflets.

As shown in FIG. 1, a heart 10 has multiple chambers including a left atrium 20 and a left ventricle 30. The mitral valve 40 separates the left atrium 20 and left ventricle 30. The mitral valve 40 includes a first (posterior) leaflet 42 and a second (anterior) leaflet 44, that are both attached to a peripheral fibrous skeleton of the heart known as the mitral valve annulus 46.

In a healthy heart, the leaflets 42 and 44 of the mitral valve 40 close the valve opening when the left ventricle 30 contracts. In such a case, blood from left ventricle 30 will be expelled from left ventricle 30 via aortic valve 50 to aorta 60. From aorta 60, blood will be supplied to parts of the body.

In some cases, leaflet 42 or 44 of mitral valve 40 or the chordae tendineae anchoring the leaflets to the papillary muscles can become floppy, elongated or rupture (flail chordae), leading to subluxation of the leaflets 42 or 44 past the annular plane during ventricular contraction, which can be referred to as mitral valve prolapse (MVP). When MVP exists, leaflets 42 and 44 of mitral valve 40 do not seal tightly. As a result, when left ventricle 30 contracts, a portion of blood from left ventricle 30 will flow backward into left atrium 20. This is known as mitral regurgitation. Regurgitation can result in heart enlargement, congestive heart failure (shortness of breath, chest pain, and edema), atrial fibrillation (irregular heartbeats), pulmonary hypertension (elevated pressure in the lungs), and death. International heart valve consensus statements recommend correction of mitral valve prolapse and elimination of mitral regurgitation before symptoms develop. Many patients delay surgery to avoid open chest surgery, post-operative complications, and the necessary six to eight weeks of postoperative recovery. Decreasing the invasiveness of MVP correction to decrease mitral regurgitation is a sought-after therapy that may save lives.

FIGS. 2A-2F illustrate example devices and a series of steps for an example method of treating MVP. The procedure generally involves a percutaneous "foldoplasty," where the redundant prolapsing segment of the prolapsing leaflet is folded or pulled down onto the ventricular or atrial surface of the mitral valve leaflet body and secured. The procedure uses a medical device system 200, which can be delivered percutaneously to the site of mitral valve 40.

Figure 2A:
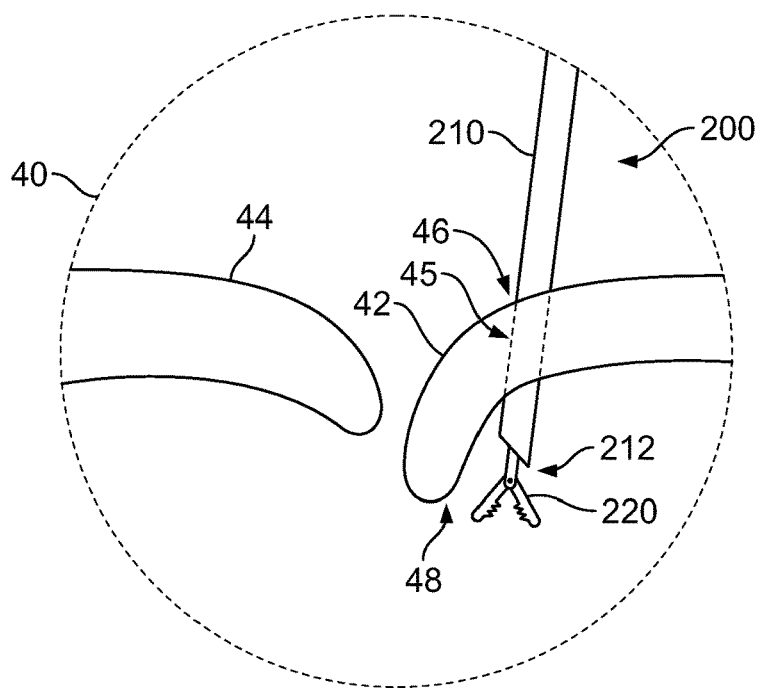
FIGS. 2A-2F are a series of figures illustrating a system and method of treating mitral valve prolapse in accordance with one example embodiment.

In FIG. 2A, a schematic of a mitral valve 40 is illustrated with its two leaflets 42 and 44. In this example, leaflet 42 is depicted as having a prolapse. Also shown is a medical device system 200 for treating the MVP. In some embodiments, medical device system 200 can approach the site of mitral valve 40 by being directed through the right atrium and into the left atrium. In some embodiments, medical device system 200 can approach the site of mitral valve 40 left ventricle (such as through the left ventricular apex) to the mitral valve site. In some embodiments, medical device system 200 can approach the site of mitral valve 40 by being directed through the right ventricle and into the left ventricle. In some embodiments, medical device system 200 can approach the site of mitral valve 40 by being directed through the aortic valve and left ventricular outflow tract and into the left ventricle. In some embodiments, medical device system can approach the site of the mitral valve 40 through the atrioventricular septum. In some embodiments, any other suitable mitral valve access path can be used. In some embodiments, a combination of such approach techniques can be used. The procedure can be performed, for example, using ultrasound visualization and/or x-ray visualization. In some embodiments, the procedure can be performed using assistance from robotics.

In some embodiments, medical device system 200 can include an introducer catheter 210. Introducer catheter 210 can have one or more lumens. In some embodiments, introducer catheter 210 can be steerable and/or exchangeable to aid in insertion and positioning of medical device system 200. Introducer catheter 210 can include a sharp-pointed distal tip (or exchangeable puncturing tip) 212 that can be used to puncture tissue such as the atrial septum and leaflet 42. In some cases, medical device system 200 can include two or more separate catheters or instruments.

As shown in FIG. 2A, in some embodiments medical device system 200 can puncture through leaflet 42 from one side of the leaflet, such that distal tip 212 of medical device system 200 is positioned on an opposite side of leaflet 42 in comparison to more the proximal portions of medical device system 200. For example, distal tip 212 of introducer catheter 210 can puncture through leaflet 42 from the top at a puncture point 46, such that distal tip 212 is positioned below leaflet 42, or vice versa. However, in some embodiments, the procedure can be performed without puncturing leaflet 42.

A second device, such as a grasping device 220 can be deployed to the area of mitral valve 40. In some cases, grasping device 220 can be located in a lumen of introducer catheter 210. In some cases, grasping device 220 can be introduced into the area of mitral valve 40 without the use of a catheter to guide it. Grasping device 220 can be any of a variety of different types of devices. For example, grasping device 220 can be straight forceps, a directional forceps, a reverse forceps, a vacuum device, a thermal device (ice or heat "welding"), and the like. In this specification, grasping device 220 may alternately be referred to as a "forceps," without limiting the types of grasping devices that are within the scope of the disclosure.

Figure 2B:
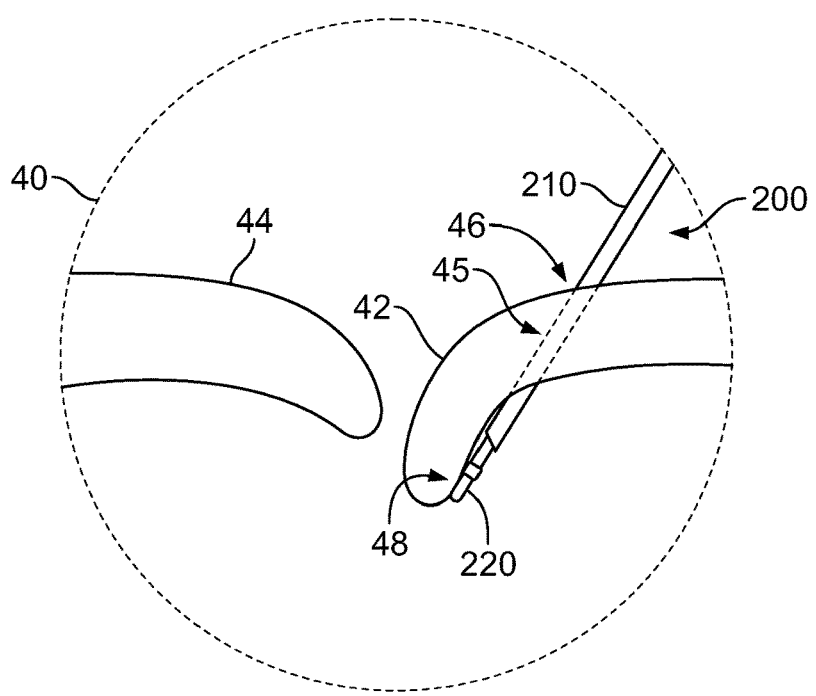

As shown in FIG. 2B, grasping device 220 can capture a prolapsing segment of leaflet 42. For example, a forceps device 220 can pinch and firmly hold a prolapsing portion 48 of leaflet 42.

Figure 2C:
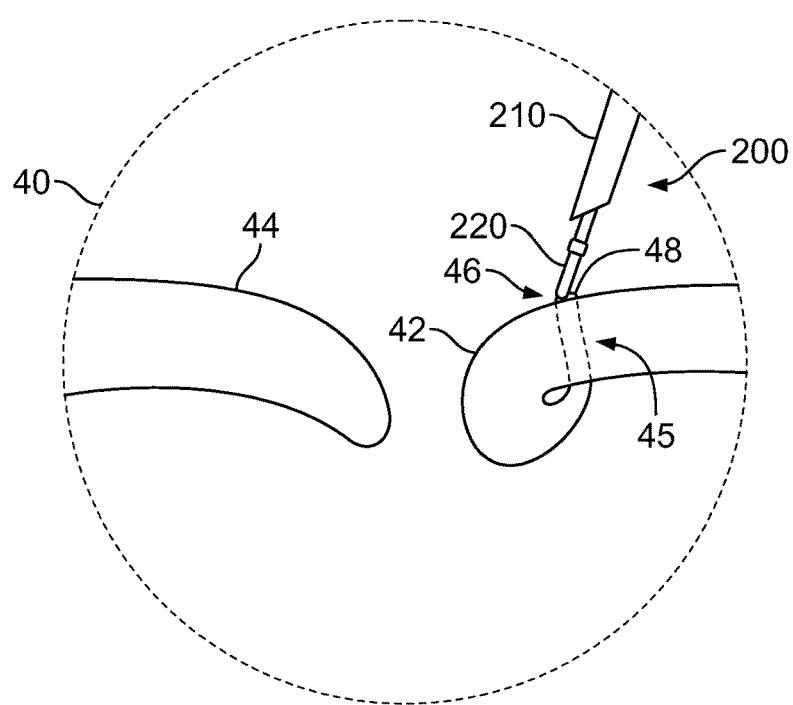

As shown in FIG. 2C, medical device system 200 can be retracted from the previous position at which grasping device 220 captured prolapsing portion 48, to a position at which prolapsing portion 48 is protruding through puncture point 46. Retracting medical device system 200 while prolapsed portion 48 is captured in grasping device 220 can pull prolapsing portion 48 through tunnel 45 in leaflet 42 that was created by the puncturing of leaflet 42 by medical device system 200. In this manner, prolapsed portion 48 of leaflet 42 can be folded onto greater leaflet 42. In some embodiments, the folding can be performed without pulling prolapsed portion 48 through tunnel 45 in leaflet 42. Rather, for example, prolapsed portion 48 can be folded using the space between leaflets 42 and 44. In either case, at least a segment of prolapsed "tip" portion 48 can be positioned on the "body" or greater portion of leaflet 42.

Figure 2D:
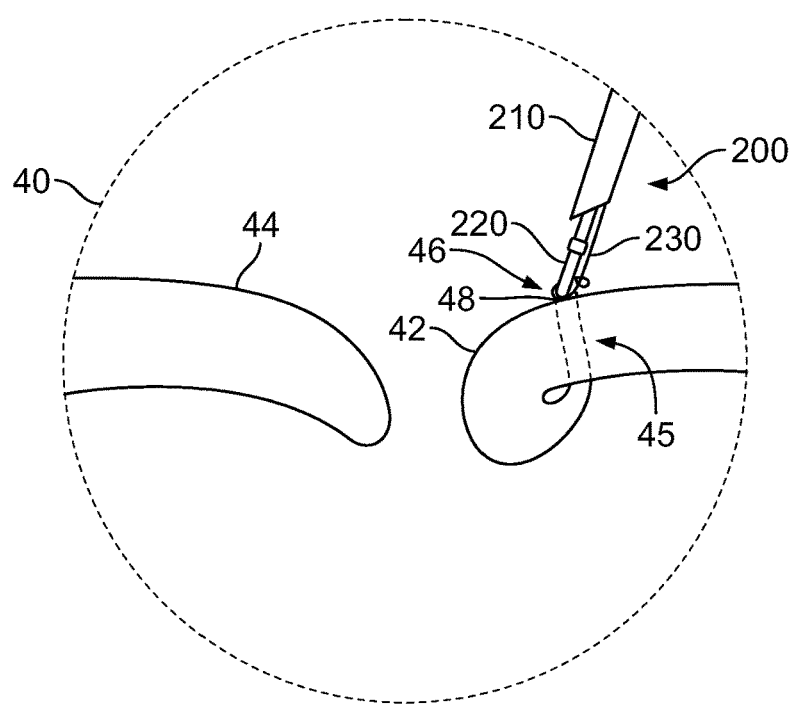

As shown in FIG. 2D, another instrument of medical device system 200 can be introduced to mitral valve 40 area to secure prolapsed portion 48 to greater leaflet 42. For example, one or more suture loops 230 can be used to secure prolapsed portion 48 in position near puncture point 46. In other embodiments, other devices and methods of securing prolapsed portion 48 to leaflet 42 can be used. For example, in some embodiments, prolapsed portion 48 can be sutured to leaflet 42 using a variety of techniques. In some embodiments, a locking or anchoring element can be used, such as a suture clip. In some embodiments, a pledget can also be utilized to increase the area over which the force from the folded prolapsed leaflet portion is distributed, thereby increasing the holding capacity resulting from the securing procedure. For example, a polymer pledget can be used in some cases.

Figure 2E:
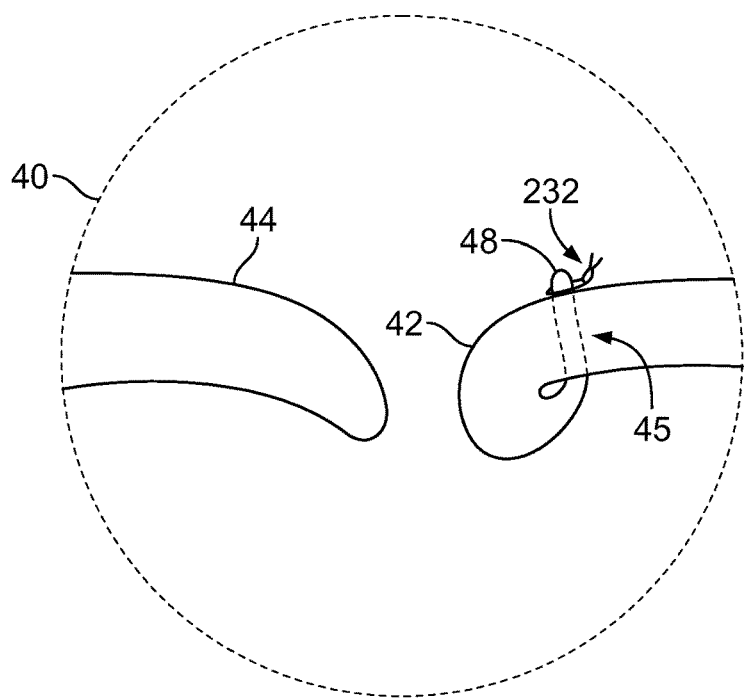

FIG. 2E depicts leaflets 42 and 44 of mitral valve 40 at the completion of the procedure. Leaflet 42 that had prolapsed portion 48 is shown as being folded onto itself. Prolapsed portion 48 of leaflet 42 is secured to the body of greater leaflet 42 by use of a securing technique such as a suture loop 232. In some cases, a pledget can be installed in between suture loop 232 and leaflet 42. In this manner, prolapsed portion 48 has been stabilized such that leaflet 42 can present a reconfigured and reinforced edge to interface with the other leaflet 44, apposing to each other at the plane of the mitral annulus, thereby eliminating MVP and mitral regurgitation.

Figure 2F:
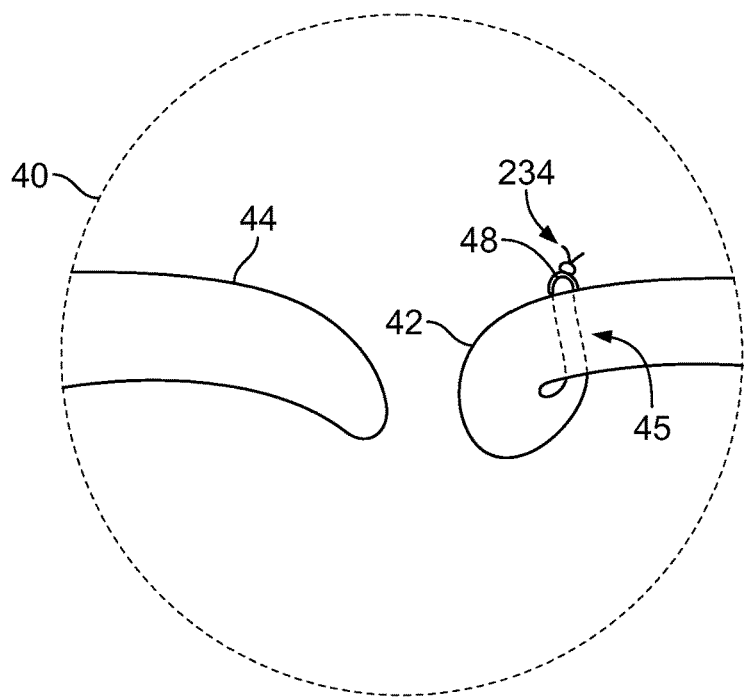

FIG. 2F also depicts leaflets 42 and 44 of mitral valve 40 at the completion of the procedure. Leaflet 42 that had prolapsed portion 48 is shown as being folded onto itself. Prolapsed portion 48 of leaflet 42 is secured to greater leaflet 42 by use of a suture 234 securing technique. In other embodiments, other securing devices and techniques can be used such as suture clips, pledgets, and other types of anchors.

Figure 3A:
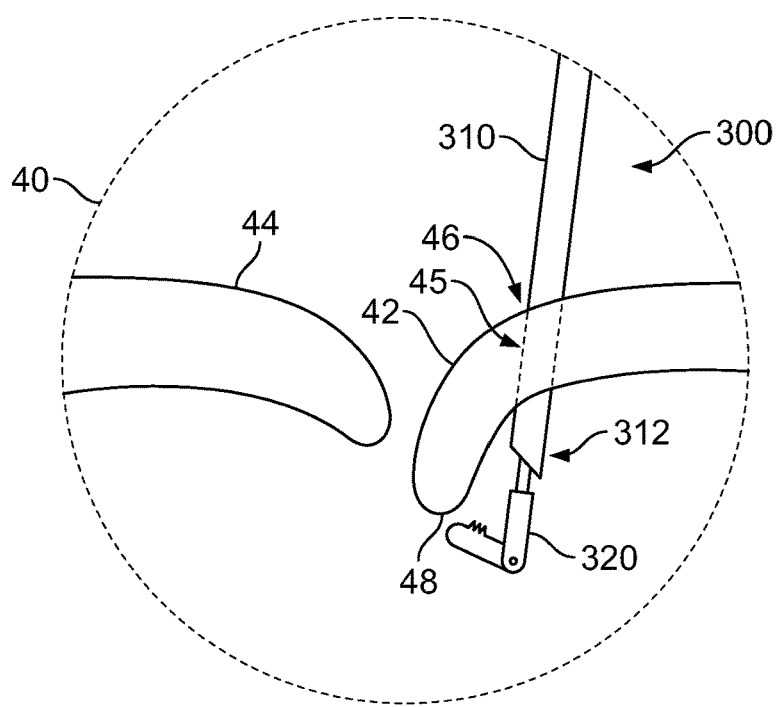
FIGS. 3A-3D are a series of figures illustrating a system and method of treating mitral valve prolapse in accordance with another example embodiment.

FIG. 3A illustrates another example of a type of medical device system 300 for treating a prolapsing leaflet 42. In this example, medical device system 300 includes a reverse or backbiting forceps 320. As shown, in some embodiments, reverse forceps 320 can be placed at the site of mitral valve 40 using an introducer catheter 310. In some cases, introducer catheter 310 may have multiple lumens that can be used for multiple devices or other purposes, such as visualization. Medical device system 300 can be routed to the site of mitral valve 40 in a number of paths as described above.

In some embodiments, introducer catheter 310 can include a sharp pointed distal tip 312 that can puncture tissue, such as atrial/ventricular walls of the heart (interatrial/interventricular or atrioventricular septums) and the leaflet of a mitral valve 40. For example, as shown in FIG. 3A, distal tip 312 can pierce leaflet 42 at a puncture point 46, and be pushed all the way through leaflet 42 to create a tunnel 45 through the leaflet—thereafter distal tip 312 of catheter 310 being positioned on the ventricular side of leaflet 42 that is opposite of puncture point 46. After the formation of tunnel 45, a grasping device can be inserted through a lumen of introducer catheter 310. As shown, the grasping device can include a reverse forceps 320, as well as other types of grasping devices as described above.

Figure 3B:
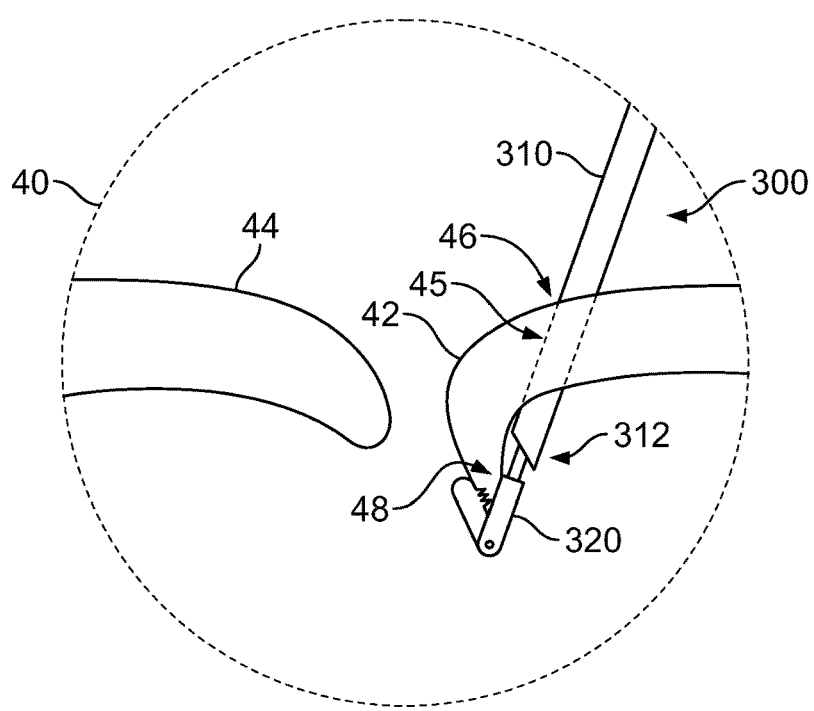

As shown in FIG. 3B, grasping device 320 can capture prolapsed tip portion 48. For example, reverse forceps 320 can pinch and hold prolapsed portion 48 to capture it. An intermediate assessment can be performed with various imaging modalities including echocardiogram, ventriculogram, CT, MRI, etc. Repositioning would therefore be facilitated at this stage to ensure optimal leaflet capture of the prolapsing leaflet tip 48. Once reverse forceps 320 have grasped prolapsed portion 48, the step of partially withdrawing medical device system 300 can be performed.

Figure 3C:
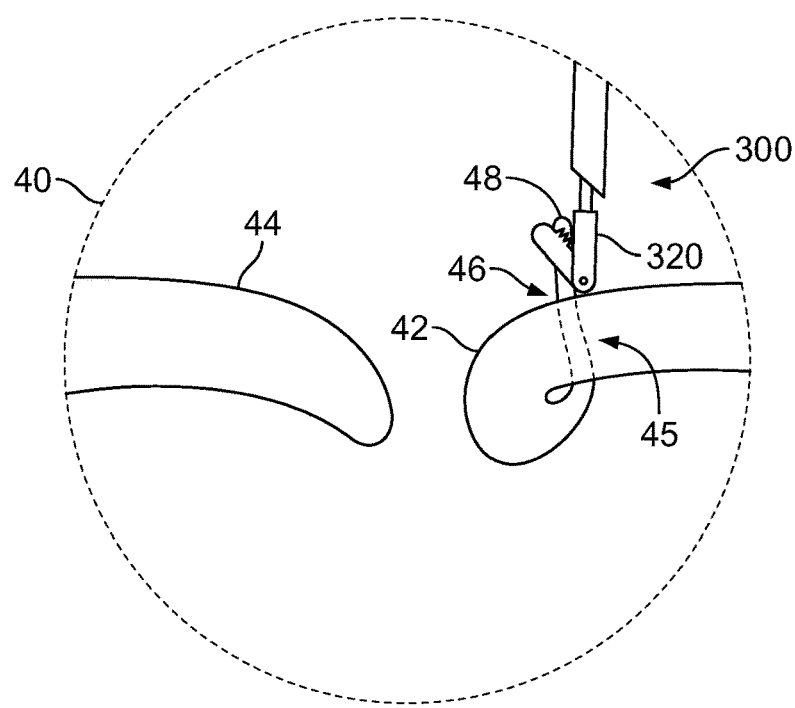

FIG. 3C depicts medical device system 300 and leaflets 42 and 44 after medical device system 300 has been withdrawn through tunnel 45 in leaflet 42. In addition, prolapsed portion 48 has also been pulled through tunnel 45 so as to fold leaflet 42 onto itself. In this position, prolapsed portion 48 is ready to be secured by medical device system 300 to greater leaflet 42.

Figure 3D:
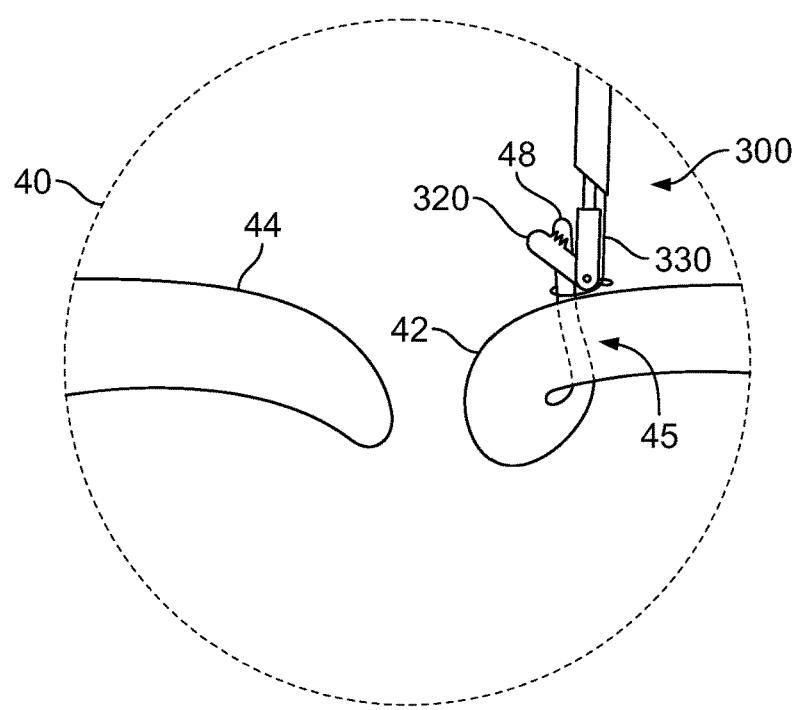

FIG. 3D depicts the step of securing the prolapsed portion 48 to greater leaflet 42. A securing device 330 can be deployed to the site of the folded leaflet 42 to perform the task of securing the prolapsed portion 48 to greater leaflet 42. For example, as shown, the securing task can be performed by a suture loop 330. As described above, a variety of other devices and techniques can be used for securing the prolapsed portion 48 to greater leaflet 42. In some embodiments, supplemental devices such as clips, pledgets, nitinol discs, and various anchoring devices can be deployed for the securing procedure.

Figure 4A:
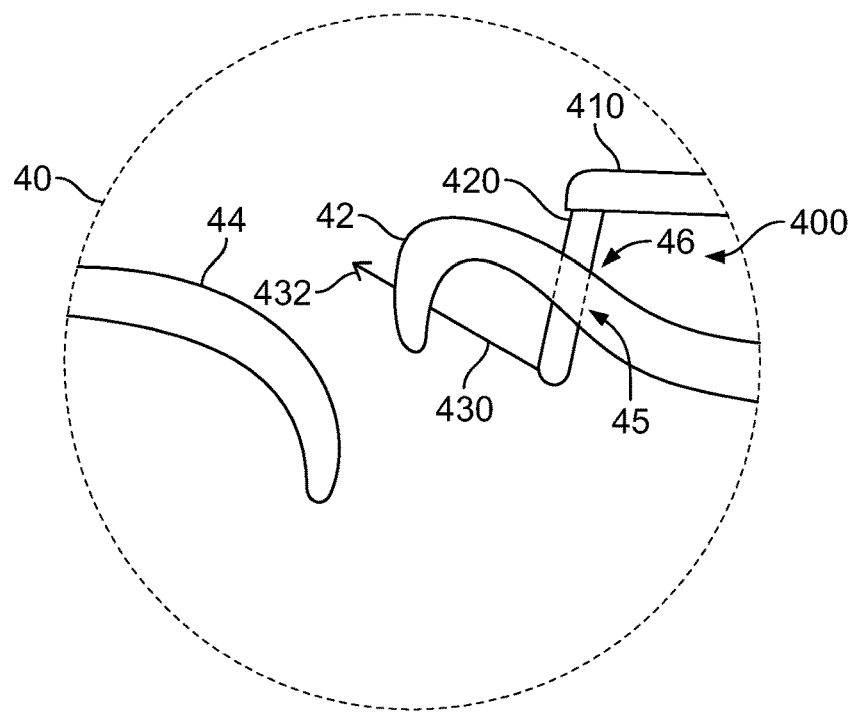
FIGS. 4A-4B are a series of figures illustrating a system and method of treating mitral valve prolapse in accordance with another example embodiment.
Figure 4B:
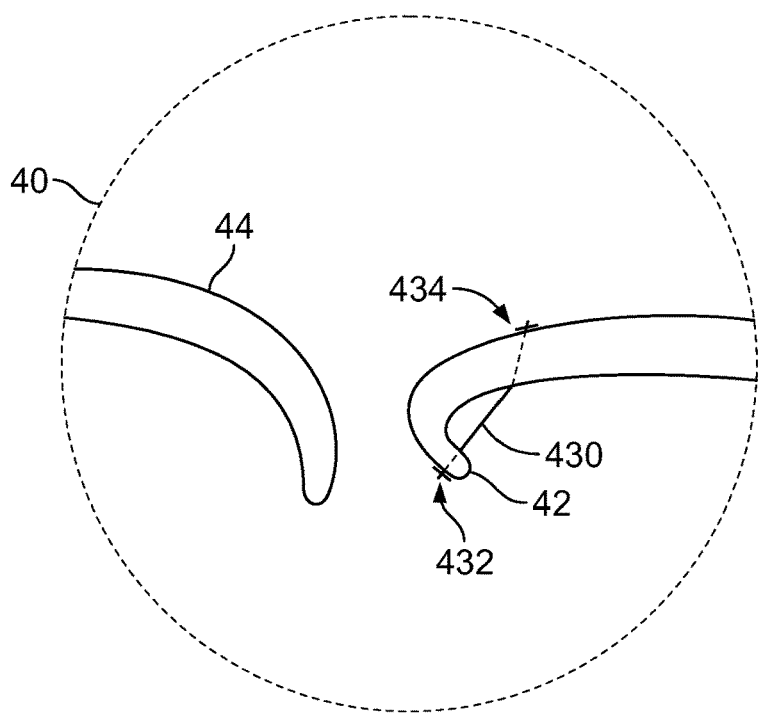

FIGS. 4A-4B illustrate a system 400 and method of treating mitral valve 40 prolapse in accordance with another example embodiment. Mitral valve 40 includes leaflets 42 and 44 as described above. Leaflet 42 is depicted as having a prolapse.

In FIG. 4A, a medical device system 400 is introduced to the site of mitral valve 40. The route of medical device system 400 can be any of the routes as described above. Medical device system 400 can include a first catheter 410, a second catheter 420, and an anchoring device 430.

First catheter 410 and second catheter 420 can be conjoined in a telescoping manner. For example, second catheter 420 can be smaller than first catheter 410 such that second catheter 420 can be at least partially positioned inside of a lumen of first catheter 410. In some embodiments, second catheter 420 can puncture leaflet 42 at puncture point 46. By pushing second catheter 420 through leaflet 42, a tunnel 45 can be formed through leaflet 42. However, in some embodiments, catheters 410 and 420 may not puncture the leaflets.

Anchor device 430, for example, can be a wire or a suture material. Anchor device 430 can be routed through the lumens of both first catheter 410 and second catheter 420. Anchor device 430 can include a distal end anchor 432. Distal end anchor 432 can be configured with a sharp point to pierce leaflet 42 (as described further below in reference to FIGS. 5A-5C and 6A-6C). As shown in FIG. 4A, anchor device 430 can pierce all the way through leaflet 42. In such a case, distal end anchor 432 can be positioned on the opposite side of leaflet 42 as compared to the rest of anchor device 430.

FIG. 4B depicts anchor device 430 in place on leaflet 42 after the removal of medical device system 400. To achieve this arrangement, second catheter 420 can be removed from tunnel 45 in leaflet 42. However, anchor device 430 can remain in tunnel 45 and in catheters 410 and 420. Next, a proximal anchor member 434 can be installed around anchor device 430 in a position in relation to leaflet 42 so that anchor device 430 is in tension, and distal end anchor 432 can retract prolapsed leaflet 42 into a less distended configuration. With proximal anchor member 434 in place, anchor device 430 can be cut at a location proximal to proximal anchor member 434 so as to result in the arrangement shown.

Figure 5A:
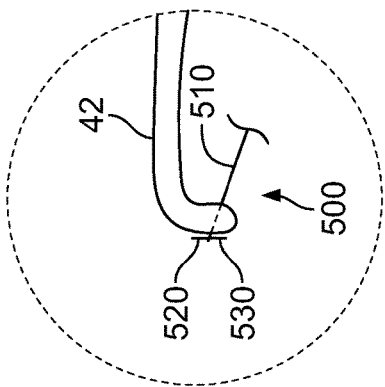
FIGS. 5A-5C are a series of figures illustrating an example anchor device and anchoring technique.
Figure 5B:
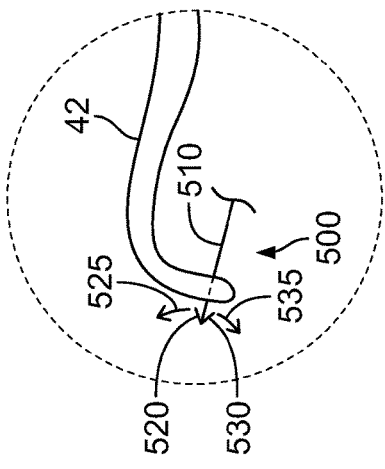
Figure 5C:
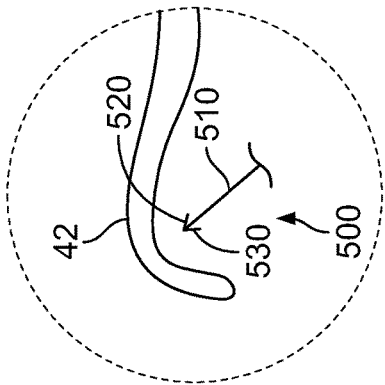

FIGS. 5A-5C illustrate an example anchor device 500 that can be used as part of a medical device system for performing the mitral valve leaflet anchoring techniques provided herein. The anchor device generally includes an elongate element 510, a first barb 520, and a second barb 530, with barbs 520 and 530 being at the distal end of anchor device 500. In some embodiments, barbs 520 and 530 can be hinged to pivot on elongate element 510. Anchor device 500 can thereby include two or more configurations. For example, anchoring device 500 can include a piercing configuration and a deployed or anchoring configuration.

As shown in FIG. 5A, anchor device 500 can be presented to leaflet 42 so that it is poised to pierce leaflet 42. At this stage, anchoring device 500 can be in the piercing configuration. As such, both barbs 510 and 520 are retracted, and the distal end of anchor device 500 resembles an arrow head.

FIG. 5B shows anchor device 500 after having pierced through leaflet 42. At this point, barbs 520 and 530 can be extended as indicated by arrows 525 and 535.

FIG. 5C depicts anchor device 500 with barbs 520 and 530 extended to provide a substantially flat surface to bear against the outer surface of leaflet 42. For example, pulling on elongate element 510 can cause barbs 520/530 to reconfigure to their anchoring configuration. At this point, elongate element 510 of anchor device 500 can be pulled further so as to retract leaflet 42 into a desired position to treat the prolapse.

Figure 6A:
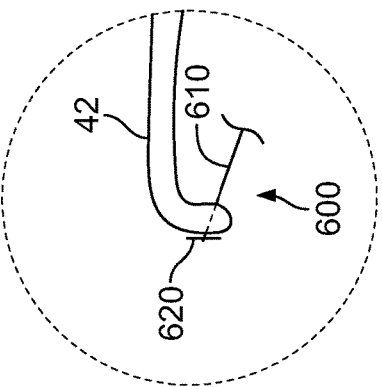
FIGS. 6A-6C are a series of figures illustrating another example anchor device and anchoring technique.
Figure 6B:
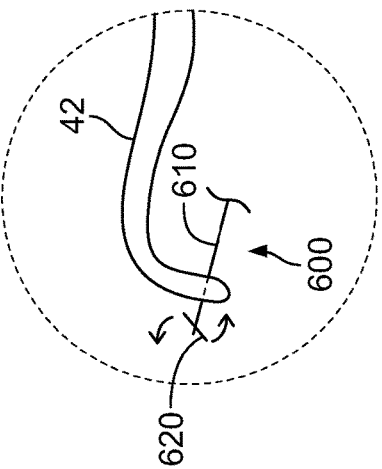
Figure 6C:
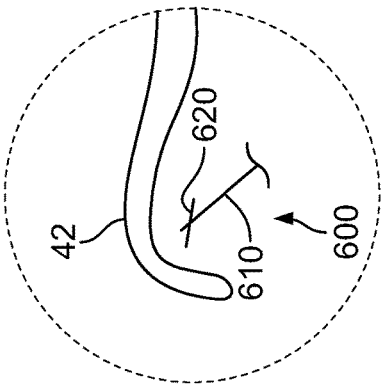

FIGS. 6A-6C illustrate another example anchor device 600 that can be used as part of a medical device system for performing a mitral valve leaflet anchoring technique provided herein. Anchor device 600 can generally include an elongate element 600 and a distal anchor 620. Distal anchor 620 can be hinged on elongate element 610 so as to have multiple configurations, such as a piercing configuration and an anchoring configuration.

In FIG. 6A anchor device 600 is positioned and configured to pierce leaflet 42. FIG. 6B shows distal anchor 620 of anchor device 600 having pierced through leaflet 42. FIG. 6C shows anchor device 600 after having tension applied to elongate element 610. In this arrangement, distal anchor 620 is in the anchoring configuration, and leaflet 42 is retracted to treat the prolapse.

Figure 7A:
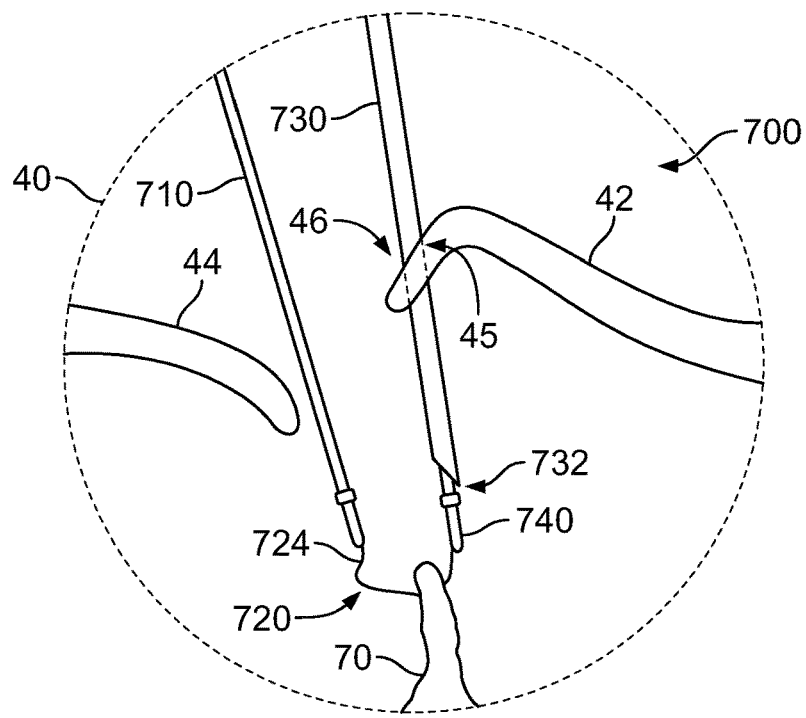
FIGS. 7A-7B are a series of figures illustrating a system and method of treating mitral valve prolapse in accordance with another example embodiment.
Figure 7B:
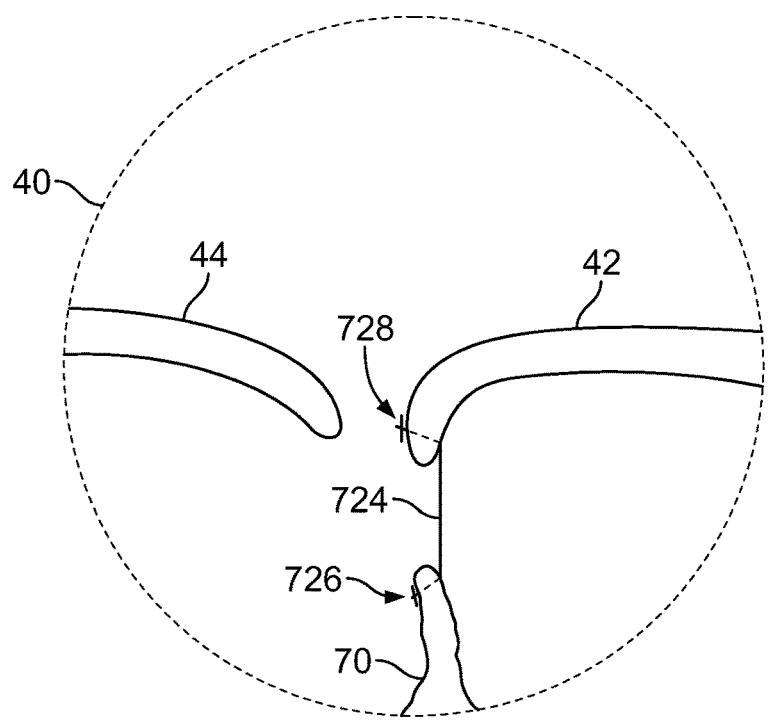

FIGS. 7A-7B illustrate another example medical device system 700 and method of treating mitral valve prolapse in accordance with another example embodiment. In general, medical device system 700 includes a first grasping device 710, a suture device 720, an introducer catheter 730, and a second grasping device 740. In this example, medical device system 700 is shown as treating a mitral valve 40 having leaflets 42 and 44. Leaflet 42 is depicted as being in a prolapsed condition. Additionally, a papillary muscle 70 is included as part of this example technique for treating MVP.

As shown in FIG. 7A, a first grasping device 710 is placed between leaflets 42 and 44. First grasping device 710 holds a suture device 720, including a needle and an anchor thread 724 that can be a wire or another type of suitable material. First grasping device 710 can be used to pierce papillary muscle 70 with suture device 720. Suture device 720 can be pushed through papillary muscle 70 such that at least the distal tip of the needle is protruding on the opposite side of papillary muscle 70.

An introducer catheter with a sharp distal tip 732 can be used to pierce leaflet 42 at a puncture site 46, and to push all the way through the thickness of leaflet 42 as shown. A tunnel 45 is thereby created. At this point, a second grasper device 740 can be inserted through a lumen of introducer catheter 730 such that the distal operative grasping member of second grasper device 740 can capture the needle of suture device 720. At this point, first grasper device 710 can release suture device 720. Then introducer catheter 730 and second grasper device 740 can be withdrawn through tunnel 45 of leaflet 42. In this manner, anchor thread 724 of suture device 720 can be pulled through tunnel 45.

FIG. 7B depicts the final position of anchor thread 724. As shown, anchor thread 724 is connected on one end to papillary muscle 70, and to leaflet 42 on the other end, thereby creating an artificial chordae. Anchor members 726 and 728 abut papillary muscle 70 and leaflet 42, respectively. These anchor members 726 and 728, for example, can be of the types described above. As shown, with anchor thread 724 in tension, papillary muscle 70 is capable of applying a force via anchor thread 724 to leaflet 42 so as to treat the prolapse condition of leaflet 42.

Figure 8A:
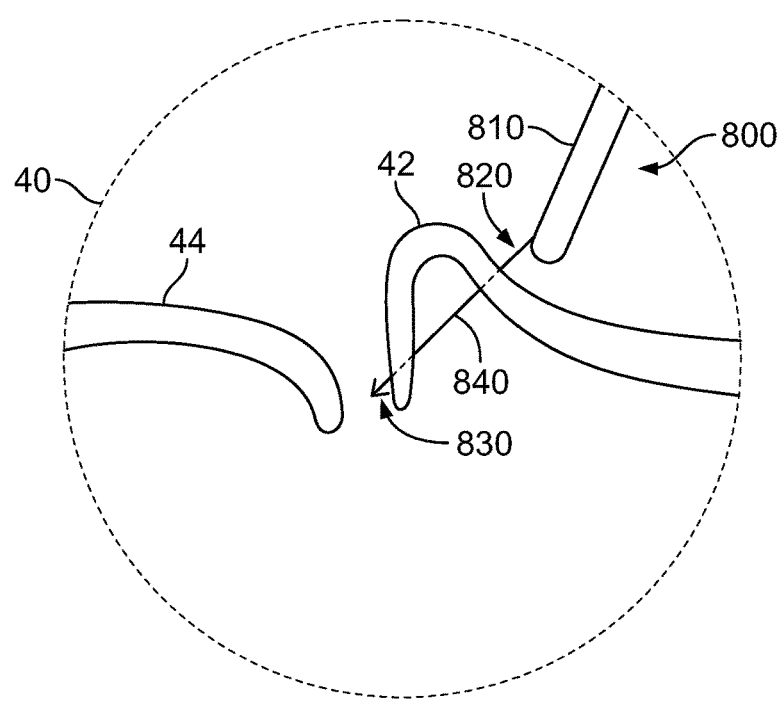
FIGS. 8A-8B are a series of figures illustrating a system and method of treating mitral valve prolapse in accordance with another example embodiment.
Figure 8B:
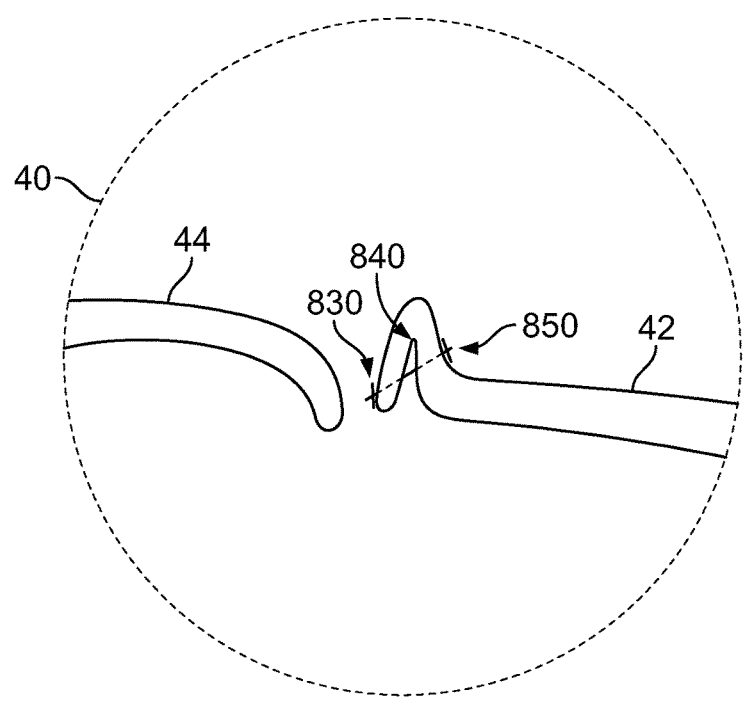

FIGS. 8A-8B illustrate another example medical device system 800 and method of treating mitral valve prolapse in accordance with another example embodiment. In general, this embodiment of an example medical device system 800 includes a catheter 810 and an anchor device 820. Medical device system 800 can be used to treat some instances of MVP. For example, in some cases, a prolapsed leaflet 42 of a mitral valve 40 can be treated by folding the wall of leaflet 42 onto itself to create a portion that has a double-thickness of leaflet 42 tissue.

As shown in FIG. 8A, a catheter 810 can be positioned near leaflet 42. An anchor device 820 can be made to extend from a lumen of catheter 810. In some embodiments, anchor device 820 can include a distal anchor member 830, such as those described in reference to FIGS. 5A-5C and 6A-6C. As shown, anchor device 820 can be pushed through two layers of leaflet 42. Distal anchor member 830 can be on the opposite side of the pierced side of the leaflet walls. Anchor thread 840 can be connected to distal anchor member 830 and located through two walls of leaflet 42.

FIG. 8B illustrates the deployed configuration of anchor device 820. As shown, distal anchor member 830 can be reconfigured to an anchoring configuration. A second anchor device 850 can be installed on the other end of anchor thread 840. Second anchor device 850 can be a suture loop, a clip, a suture to attach to the leaflet, and so on as described above. Second anchor device 850 can be installed such that the anchor thread is in tension. Thus, the two layers of leaflet 42 can be pulled together as shown so as to treat the prolapse condition of leaflet 42.

Figure 9A:
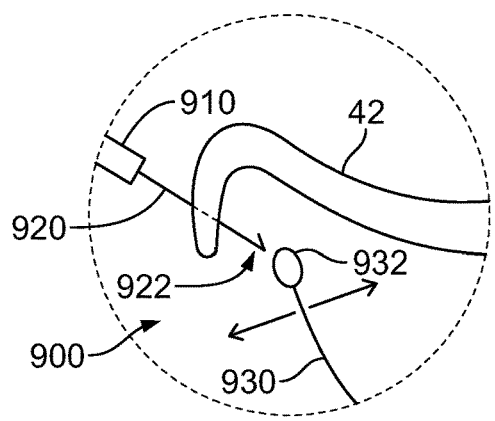
FIGS. 9A-9C are a series of figures illustrating a system and method of treating mitral valve prolapse in accordance with another example embodiment.
Figure 9B:
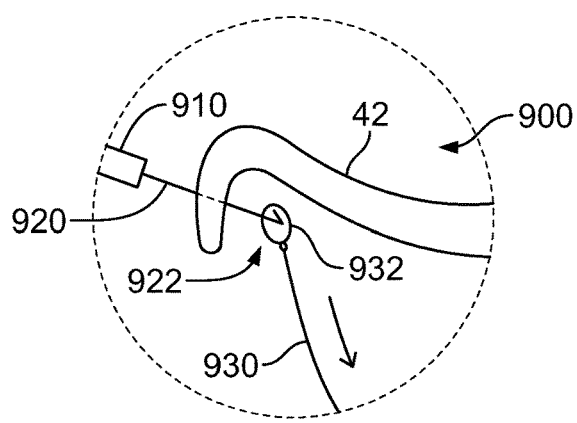
Figure 9C:
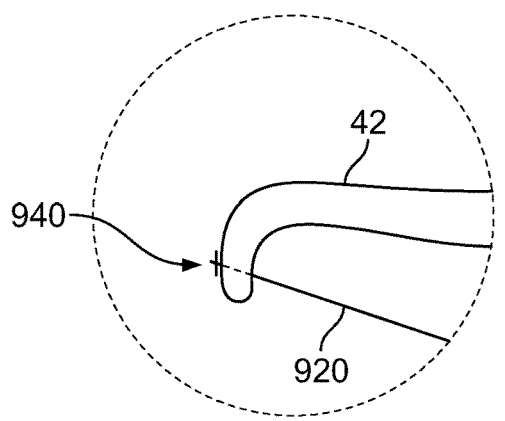

FIGS. 9A-9C illustrate a medical device system 900 and method of treating mitral valve prolapse in accordance with another example embodiment. This example is a method where a dual approach can be used to secure prolapsed leaflet 42 to the apex or ventricular septum of the left ventricle. In this method, a first catheter 910 approaches as per the embodiments provided herein, and pierces leaflet 42 with a wire anchor device 920 with a hook 922 at the distal end of wire anchor device 920. A second catheter (not shown) is placed in the right ventricle or outside the apex of the left ventricle. The second catheter can place a capture wire 930 with a loop 932 into the left ventricle via the ventricular septum or apex of the left ventricle. The second catheter can position the wire at the bottom surface of leaflet 42 as shown.

As depicted in FIGS. 9B and 9C, wire loop 932 can capture hook 922. Capture wire 930 can then pull wire anchor device 920 back to the left ventricular septal wall, or the wall of the apex. A suture with an anchoring element 940 can be attached to the proximal end of wire anchor device 920. As wire anchor device 920 is pulled, wire 920 travels through leaflet 42 until anchoring element 940 stops at the surface of leaflet 42. Capture wire 930 is pulled to final position at the left ventricular septum or left ventricle apex. Capture wire 930 can pull wire 920 to such a distal position, at which point a second anchoring element (not shown) can be installed to fix wire 920 in place.

Figure 10A:
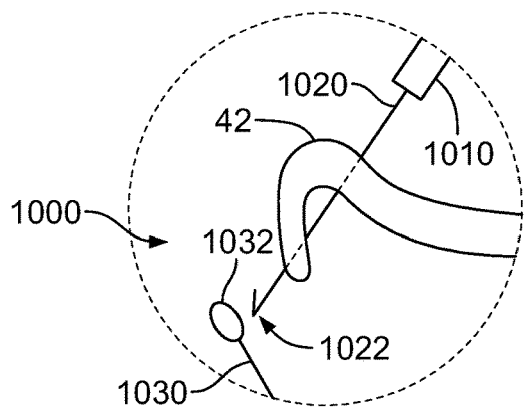
FIGS. 10A-10C are a series of figures illustrating a system and method of treating mitral valve prolapse in accordance with another example embodiment.
Figure 10B:
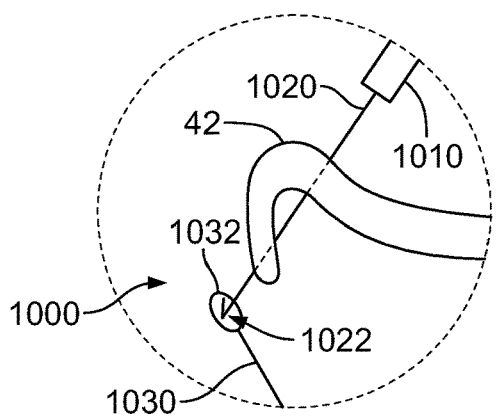
Figure 10C:
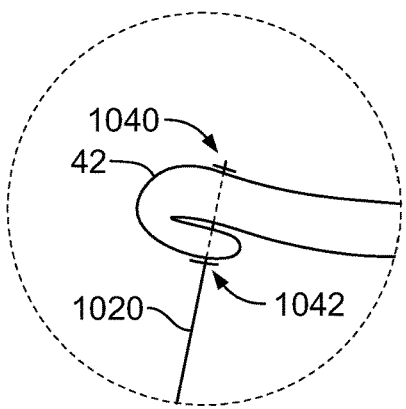

With reference to FIGS. 10A-10C, a series of figures illustrate a system 1000 for treating a leaflet 42 with MVP in accordance with another example embodiment. The system 1000 performs a treatment including a foldoplasty and the installation of an artificial chordae.

System 1000 includes a catheter 1010, an artificial chordae 1020, and a capture wire 1030. Catheter 1010 can access the site of leaflet 42 using any suitable path as described above, e.g., via the intraatrial septum. Catheter 1010 can deliver artificial chordae 1020.

With reference to FIG. 10A, an artificial chordae 1020 includes a piercing tip 1022. In some embodiments, piercing tip 1022 can penetrate leaflet 42 twice so as to facilitate a foldoplasty technique where the redundant prolapsing segment of leaflet 42 is folded or pulled onto the ventricular or atrial surface of mitral valve leaflet 42 and secured.

In some cases, a capture wire 1030 can approach mitral valve leaflet 42 from the opposite side as catheter 1010. Capture wire 1020 can include a wire loop 1032 that can act as a lasso to capture and engage piercing tip 1022 as shown in FIG. 10B. In some cases, capture wire 1030 can be passed through a septum such as the ventricular septum, and in some cases through a papillary muscle. Such anatomical structures can be used as anchorages for artificial chordae 1020. With capture wire 1020 engaged with artificial chordae 1020, capture wire 1030 can be pulled to draw artificial chordae 1020 through leaflet 42 and through the septum and/or papillary muscle anchorage location.

With reference to FIG. 10C, in some cases, a pair of pledgets 1040 and 1042 can be installed on folded leaflet 42 to contain leaflet 42 in the folded configuration. In some cases, sutures, clips, nitinol discs, and the like can be used rather than or in addition to pledgets. Artificial chordae 1020 can be anchored in a papillary muscle, septum, ventricular or atrial free wall, a combination of a papillary muscle and septum or wall, or any other suitable anatomical anchorage location. Artificial chordae 1020 can be cut to remove extra length.

Figure 11A:
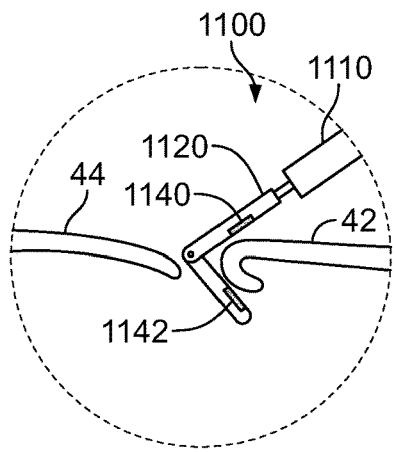
FIGS. 11A-11F are a series of figures illustrating systems and methods of treating mitral valve prolapse in accordance with other example embodiments.
Figure 11B:
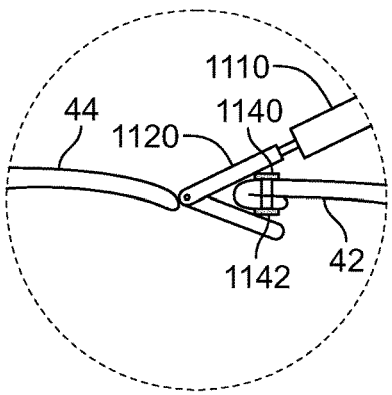

With reference to FIGS. 11A-11F, this series of figures illustrate systems and methods of treating MVP in accordance with additional example embodiments. For example, FIGS. 11A and 11B illustrate a system 1100 including a catheter 1110 and a grasping device 1120. Grasping device 1120 includes a first clip 1140 and a second clip 1142 that are releasably coupled to the jaws of grasping device 1120. In some cases, grasping device 1120 can be introduced to the mitral valve via the left atrium and positioned such that closure of the jaws of grasping device 1120 will fold the prolapsed portion of leaflet 42.

As shown in FIG. 11B, grasping device 1120 can be closed onto leaflet 42 to fold an edge of leaflet 42 on itself. The closure of grasping device 1120 can bring first clip 1140 into engagement with second clip 1142. In some cases, first clip 1140 and second clip 1142 can couple to each other using a mechanical latching mechanism. For example, in some cases, one of the clips 1140 or 1142 can have one or more barbed projections and the other clip 1140 or 1142 can have complimentary receptacles in which the barbed projections can be locked. Any suitable coupling mechanism can be used to engage first clip 1140 to second clip 1142. In some cases, sutures, screws, anchors, barbs and the like can be used instead of clips 1140 and 1142.

Figure 11C:
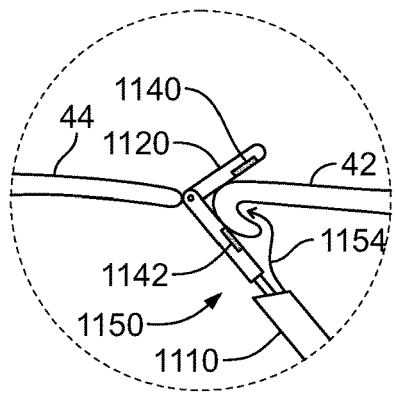
Figure 11D:
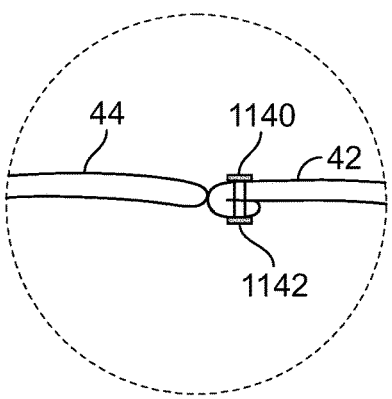

With reference to FIG. 11D, first clip 1140 and second clip 1142 are shown in an engaged configuration on leaflet 42. The configuration of first clip 1140 and second clip 1142 can be referred to herein as a "jawless clip." That is, first clip 1140 and second clip 1142 do not include a hinge or jaw to couple them together. Therefore, the folded edge of posterior leaflet 42 that is presented to the anterior leaflet 44 can be free from obstructions related to the clip. In some cases, the use of this foldoplasty system and technique is the extent of the MVP treatment provided. In some cases, this foldoplasty system and technique can be augmented to include installation of artificial chordae as described herein.

With reference to FIG. 11C, another example system 1150 for performing a foldoplasty to treat MVP of a leaflet 42 is provided. System 1150 can include a catheter 1110 and a grasping device 1120. Grasping device 1120 can include a first clip 1140 and a second clip 1142 that are releasably coupled to the jaws of grasping device 1120 as described herein. In some cases, grasping device 1120 can be introduced to the mitral valve via the left ventricle, and positioned such that closure of the jaws of grasping device 1120 will fold the prolapsed portion of leaflet 42.

In some cases, system 1150 can include a bending device 1154 delivered via catheter 1110. Bending device 1154 can cooperate with grasping device 1120 to induce a fold in the prolapsed portion of leaflet 42 prior to or at the time of closure of grasping device 1120. Bending device 1154 can have a blunt distal tip and can comprise any suitable material, e.g., nitinol, stainless steel, and polymeric materials. In some cases, bending device 1154 can be steerable. In some cases, a portion of bending device 1154 can remain implanted between the folds of leaflet 42. In some cases, bending device 1154 can be removed from folded leaflet 42. System 1150 can apply a jawless clip as shown in FIG. 11D.

Figure 11E:
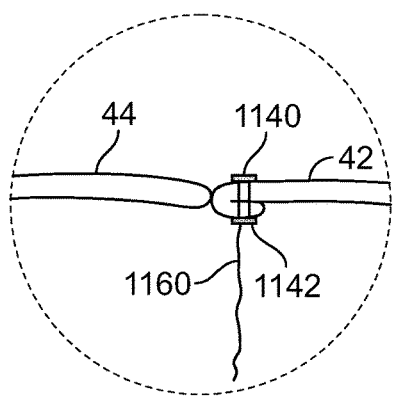
Figure 11F:
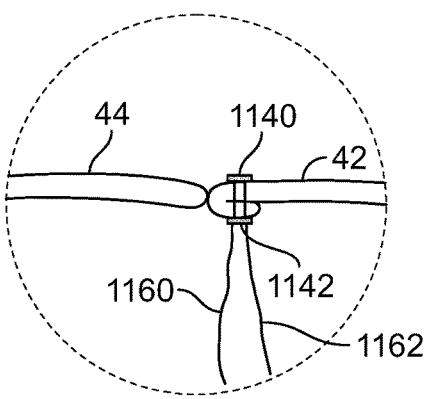

With reference to FIGS. 11E and 11F, jawless clips can include one or more artificial chordae 1160 and 1162. In some cases, artificial chordae 1160 and 1162 can be sutures or wires. Artificial chordae 1160 and 1162 can be anchored to various areas of the heart so as to stabilize a mitral valve leaflet.

With reference to FIG. 11E, in some cases, a single artificial chordae 1160 can be attached to clip 1140 or 1142. In some cases, artificial chordae 1160 can be pre-attached to clip 1140 or 1142 as delivered by grasping device 1120. In some cases, artificial chordae 1160 can be attached to clip 1140 or 1142 after installation of the jawless clip.

With reference to FIG. 11F, in some cases, two artificial chordae 1160 and 1162 can be attached to clip 1140 or 1142. As will be described further below in reference to FIG. 15A, two artificial chordae 1160 and 1162 can be used to anchor to two different locations within the heart.

Figure 12A:
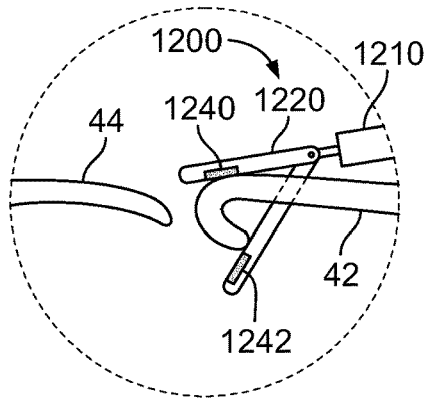
FIGS. 12A and 12B are a series of figures illustrating a system and method of treating mitral valve prolapse in accordance with another example embodiment.
Figure 12B:
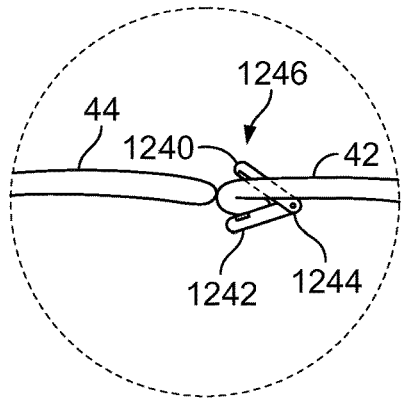

With reference to FIGS. 12A and 12B, a system 1200 for performing a foldoplasty to treat MVP of a leaflet 42 is provided. System 1200 can include a catheter 1210 and a grasping device 1220. In some cases, grasping device 1220 can be introduced to the mitral valve via the left atrium (e.g., an intraatrial septum approach) and positioned such that closure of the jaws of grasping device 1220 will fold the prolapsed portion of leaflet 42. In some cases, other suitable access paths can be utilized, e.g., via the aorta or intraventricular septum. In some cases, one jaw of grasping device 1220 can penetrate leaflet 42 as shown.

In some cases, grasping device 1220 can include a first clip 1240 and a second clip 1242 that are releasably coupled to the jaws of grasping device 1220, comprising a jawless clip as described herein. In some embodiments, the penetration of leaflet 42 by one jaw of grasping device 1220 can enable a clip with a hinged portion 1244 to be used without obstructing the interface between leaflets 42 and 44. For example, FIG. 12B depicts a hinged clip 1246 installed on leaflet 42. In some cases, such clips can include one or more artificial chordae.

Figure 13A:
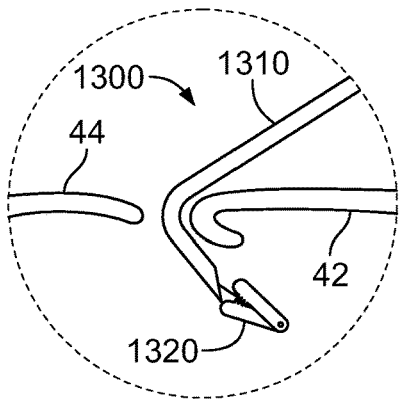
FIGS. 13A-13D are a series of figures illustrating a system and method of treating mitral valve prolapse in accordance with another example embodiment.
Figure 13B:
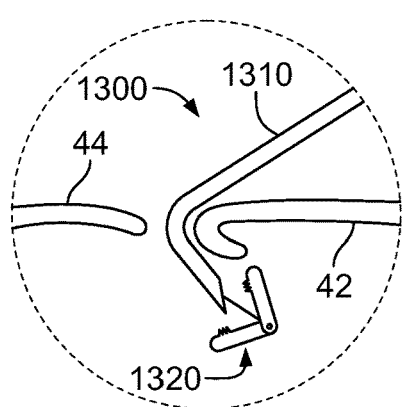
Figure 13C:
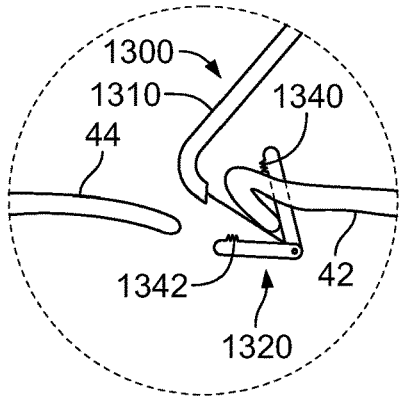

With reference to FIGS. 13A-13D, a system 1300 for performing a foldoplasty to treat MVP of a leaflet 42 is provided. System 1300 can include a catheter 1310 and a grasping device 1320. As shown in FIG. 13A, in some cases, grasping device 1320 can approach the mitral valve via the left atrium (e.g., an intraatrial septum approach) and be positioned such that closure of the jaws of grasping device 1320 will fold the prolapsed portion of leaflet 42. In some cases, other suitable approaches can be utilized, e.g., via the aorta or intraventricular septum. In some cases, one jaw of grasping device 1320 can penetrate leaflet 42 as shown in FIG. 13C.

Figure 13D:
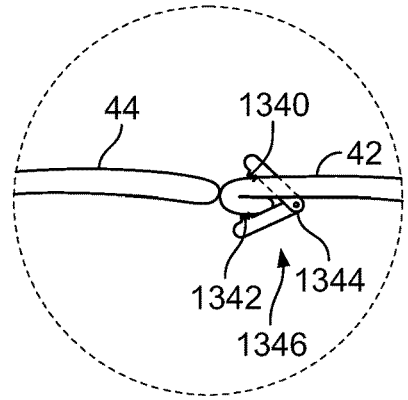

In some cases, grasping device 1320 can include a first clip 1340 and a second clip 1342 that are releasably coupled to the jaws of grasping device 1320, comprising a jawless clip as described above. In some embodiments, the penetration of leaflet 42 by one jaw of grasping device 1320 can enable a clip with a hinged portion 1344 to be used without obstructing the interface between leaflets 42 and 44. For example, FIG. 13D depicts a hinged clip 1346 installed on leaflet 42. In some cases, such clips can include one or more artificial chordae.

Figure 14A:
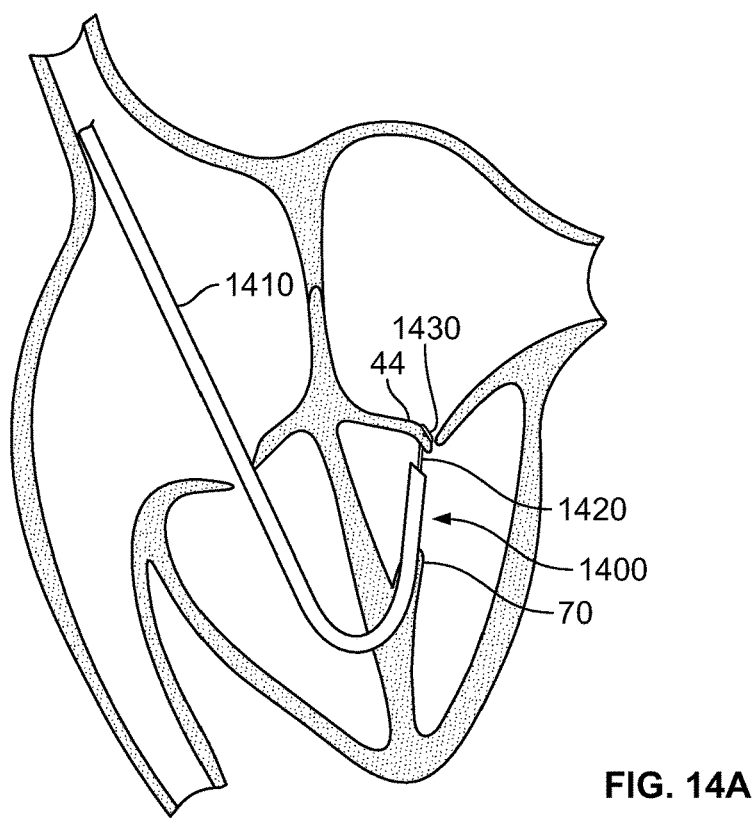
FIGS. 14A and 14B are a series of figures illustrating a system and method of treating mitral valve prolapse in accordance with another example embodiment.
Figure 14B:
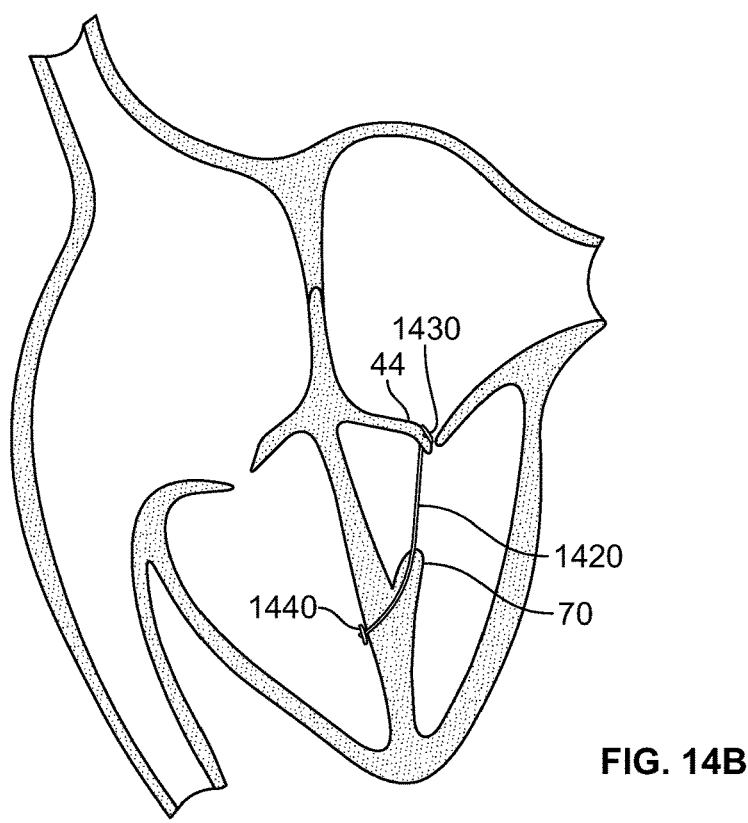

With reference to FIGS. 14A and 14B, a system 1400 for installing an artificial chordae is depicted. The artificial chordae can be attached to either or both of the anterior and posterior valve leaflets, and in any location thereon. Therefore, it should be understood that the figures are provided as examples of the techniques, and that such techniques can be applied to either or both leaflets. System 1400 can include a catheter 1410 and an artificial chordae 1420. In some cases, an intraventricular septum approach by catheter 1410 can be used. In some cases, other suitable approaches can be used. In some cases, catheter 1410 can be advanced through a papillary muscle 70.

In some cases, artificial chordae 1420 can be used to pierce leaflet 44 and a distal end of artificial chordae 1420 can be attached to leaflet 44 using a first pledget 1430, or a suture, clip, anchor, etc. as described above. In some cases, catheter 1410 can deliver a lasso device to couple with a pre-installed artificial chordae, such as an artificial chordae attached to a foldoplasty clip as described herein in reference to FIGS. 11E and 11F.

Catheter 1410 can be retracted to the right side of the heart, and a second pledget 1440 can be installed on the right ventricle side of the ventricular septum. Prior to finalizing the placement of the second pledget 1440, the tension on artificial chordae 1420 can be optimized. To optimize the tension on artificial chordae 1420, an intermediate assessment can be performed using various imaging modalities including echocardiogram, ventriculogram, CT, MRI, etc. to monitor regurgitation levels at various tensions. The desired tension of artificial chordae 1420 can be determined based on minimizing regurgitation.

Figure 15A:
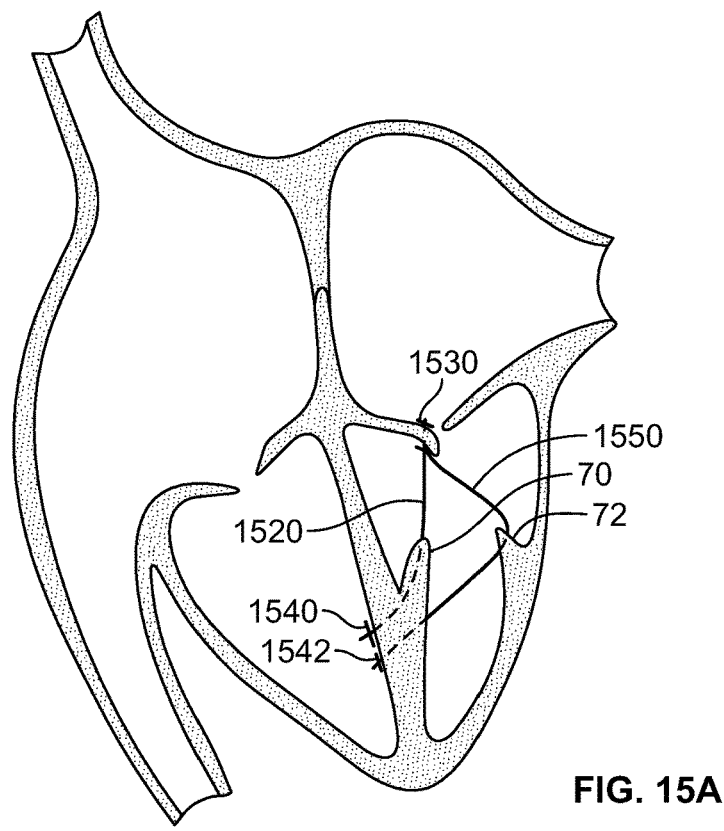
FIGS. 15A and 15B are a series of figures illustrating a system and method of treating mitral valve prolapse in accordance with another example embodiment.
Figure 15B:
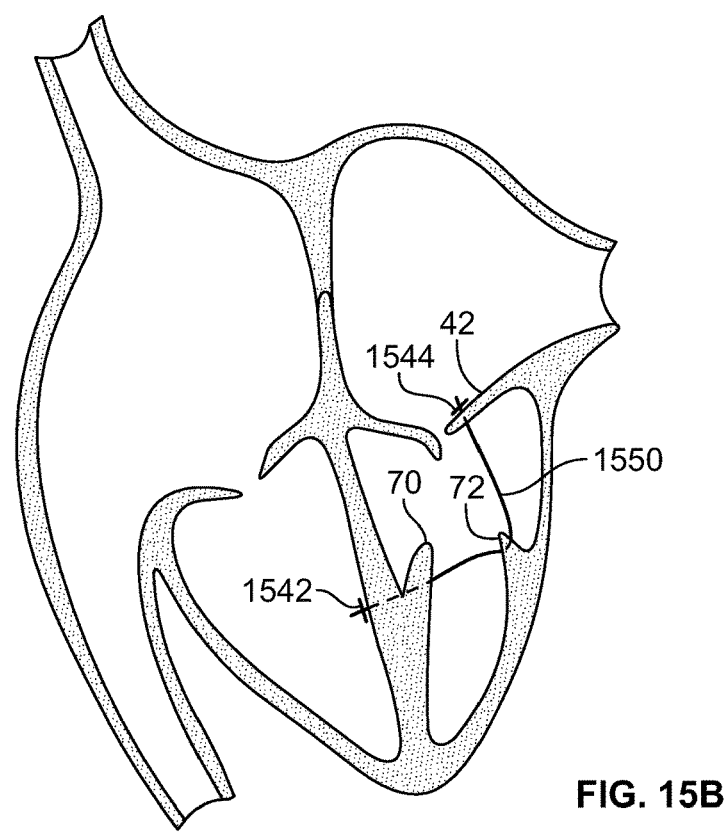

With reference to FIGS. 15A and 15B, additional exemplary configurations of artificial chordae are provided. The artificial chordae can be attached to either or both of the anterior and posterior valve leaflets, and in any location thereon. Therefore, it should be understood that the figures are provided as examples of the techniques, and that such techniques can be applied to either or both leaflets. In FIG. 15A, two artificial chordae 1520 and 1550 are attached to a foldoplasty clip 1530. Artificial chordae 1520 can be routed through a first papillary muscle 70 and anchored on the wall of the right ventricle using a pledget 1540. A second artificial chordae 1550 can be routed through a second papillary muscle 72 and anchored on the wall of the right ventricle using a pledget 1542.

In FIG. 15B, a single artificial chordae 1550 is attached to leaflet 42 using a pledget 1544, which could also be a foldoplasty clip, suture, anchor, barb, and so on. Artificial chordae 1550 can be routed through a papillary muscle 72, then through another papillary muscle 70 and anchored on the wall of the right ventricle using a pledget 1542. Any suitable anchorage location can be used, e.g., the left ventricle free wall or a papillary muscle.

Figure 16A:
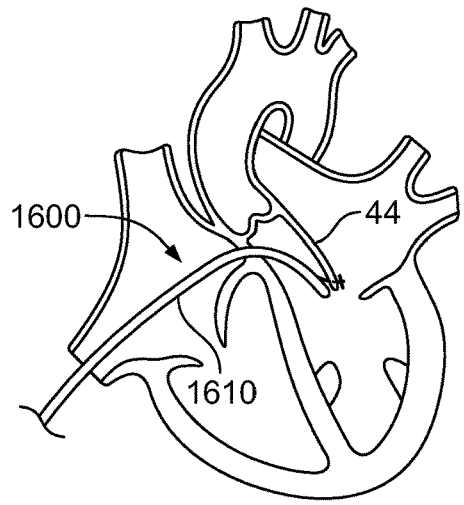
FIGS. 16A-16C are a series of figures illustrating a system and method of treating mitral valve prolapse in accordance with another example embodiment.
Figure 16B:
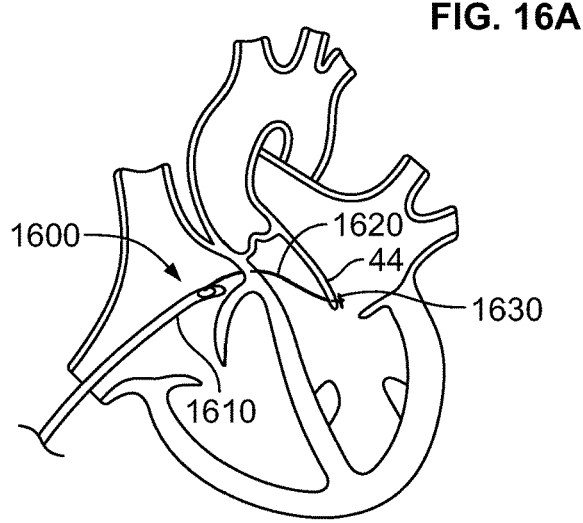
Figure 16C:
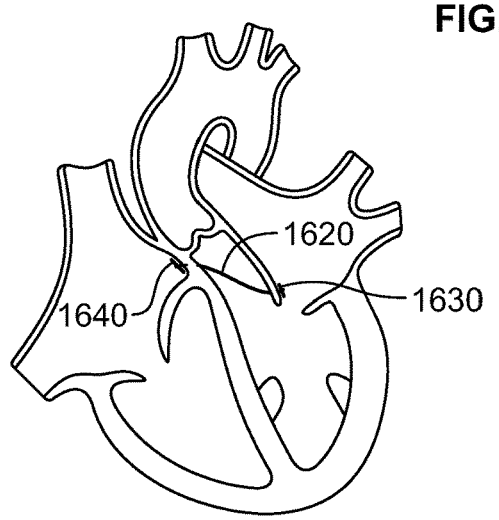

With reference to FIGS. 16A-16C, a system 1600 for installing an artificial chordae 1620 using an atrioventricular septum approach is illustrated. The artificial chordae can be attached to either or both of the anterior and posterior valve leaflets, and in any location thereon. Therefore, it should be understood that the figures are provided as examples of the techniques, and that such techniques can be applied to either or both leaflets. System 1600 includes a catheter 1610 which can approach a mitral valve leaflet 44. Artificial chordae 1620 can be attached to leaflet 44 using a clip 1630, or a pledget, a nitinol disc, suture, or other suitable device. Catheter 1610 can be retracted such that the distal tip of catheter 1610 is in the right atrium. A second anchoring device, such as a pledget 1640, can be installed on the wall of the atrioventricular septum in the right atrium. The tension on artificial chordae 1620 can be adjusted to minimize mitral valve regurgitation prior to the final placement of pledget 1640.

Figure 17:
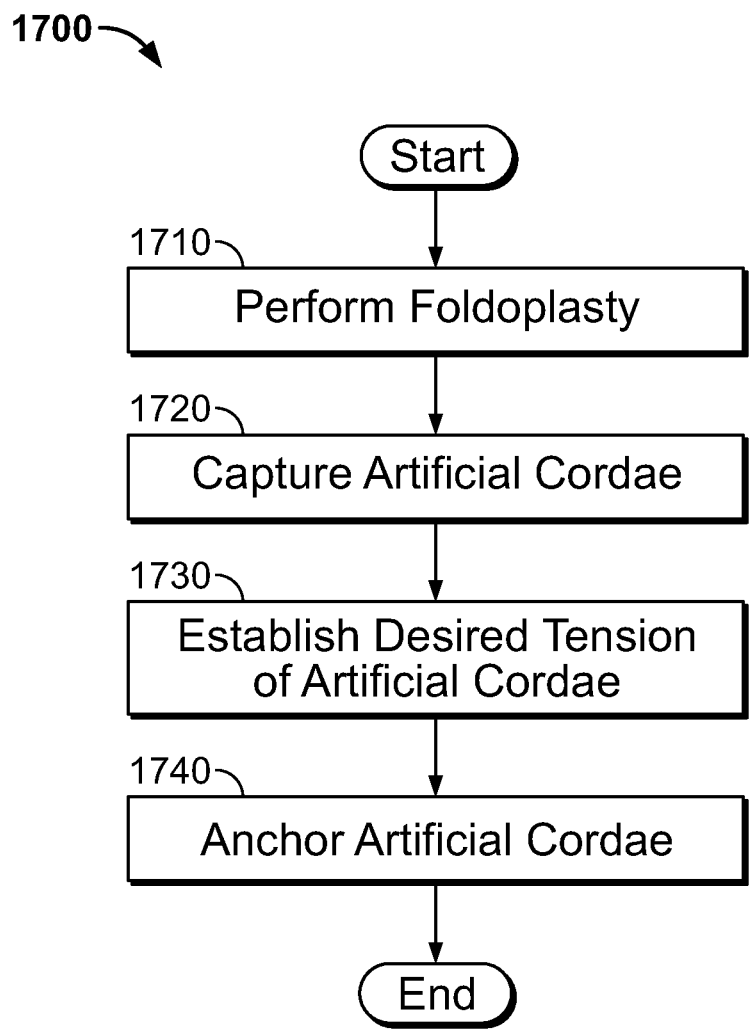
FIG. 17 is a flowchart describing a method of treating mitral valve prolapse using the systems provided herein.

With reference to FIG. 17, an exemplary process 1700 for treating MVP is provided. Process 1700 can be performed in accordance with many of the systems and techniques described herein.

At operation 1710, a foldoplasty is performed. For example, systems and techniques such as those provided herein in reference to FIGS. 2A-2F, 3A-3D, 4A-4B, 11A-11F, 12A-12B, and 13A-13D can be utilized for the foldoplasty procedure. In some cases, a clip can be installed to fold a prolapsed leaflet. In some cases, the clip can be a jawless clip. Various other devices and techniques, such as those described herein, can also be used to perform the foldoplasty. The technique can include the attachment of an artificial chordae to the leaflet. In some cases, the artificial chordae can be pre-attached to a clip used to perform the foldoplasty.

At operation 1720, an artificial chordae attached to the prolapsed leaflet is captured. For example, the artificial chordae can be captured by a forceps or by a lasso device. The device used to capture the artificial chordae can be located so as to enable the anchoring of the artificial chordae in the desired anatomical location. For example, if it is desired to attach the artificial chordae to a papillary muscle, the device used to capture the artificial chordae can be routed through the papillary muscle. In that case, when the device is retracted the artificial chordae will be pulled through the papillary muscle as desired.

At operation 1730, the tension of the artificial chordae is established. This operation can be performed by monitoring the regurgitation of the mitral valve while adjusting the tension of the artificial chordae. In some cases, the regurgitation can be monitored using various imaging modalities including echocardiogram, ventriculogram, CT, MRI, etc. to monitor regurgitation levels at various tensions. The tension of the artificial chordae can be established based on minimizing regurgitation.

At operation 1740, the artificial chordae can be anchored in the desired location to maintain the optimum tension of the artificial chordae. In some cases, the anchoring can be performed using a pledget on the opposite side of a septum. In some cases, an anchor device, such as a helical anchor, can be used to anchor the artificial chordae in tissue, such as the ventricular wall.

In some cases, both anterior and posterior mitral valve leaflets can be repaired using the systems and methods provided herein. For example, a foldoplasty can be performed on one or both the anterior and posterior mitral valve leaflets. In some cases, artificial chordae can be installed for one or both the anterior and posterior mitral valve leaflets.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various systems and components in the embodiments described above should not be understood as requiring such separation in all embodiments, and it should be understood that the described components and systems can generally be integrated together in a product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method for treating mitral valve prolapse, wherein said method comprises: (a) approaching a prolapsed leaflet using a minimally invasive catheter technique, (b) capturing an edge segment of the prolapsed leaflet using a grasping device, (c) repositioning the edge segment onto an atrial or ventricular surface of a body of the prolapsed leaflet, and (d) securing the edge segment to the atrial or ventricular surface of the body of the prolapsed leaflet using an attachment device, wherein the repositioning creates a fold in the prolapsed leaflet that results in tissue from the body of the prolapsed leaflet becoming a reconfigured edge of the prolapsed leaflet, wherein the reconfigured edge made of tissue from the body of the prolapsed leaflet apposes and coapts with an opposing leaflet to reduce mitral valve regurgitation and a longitudinal axis of the fold is parallel to a line of coaptation between the prolapsed leaflet and the opposing leaflet.

2. The method of claim 1, wherein the prolapsed leaflet is constrained in a folded configuration as a result of the securing the edge segment onto the atrial or ventricular surface of the body of the prolapsed leaflet using the attachment device.

3. The method of claim 1, wherein said attachment device comprises a suture or a clip device.

4. The method of claim 3, wherein the suture or the clip device comprises one or more artificial chordae extending therefrom.

5. The method of claim 4, further comprising anchoring the one or more artificial chordae to other tissue spaced apart from the prolapsed leaflet.

6. The method of claim 1, wherein said repositioning comprises positioning at least a portion of said edge segment within a channel formed in said prolapsed leaflet.

7. The method of claim 1, wherein said approaching comprises piercing an interatrial septum.

8. The method of claim 1, wherein said approaching comprises piercing a heart apex.

9. The method of claim 1, wherein the grasping device comprises two jaws, and
wherein, during the repositioning, one jaw of the two jaws is penetrating through the body of the prolapsed leaflet.

* * * * *